US009983139B2

(12) United States Patent
Cooper

(10) Patent No.: US 9,983,139 B2
(45) Date of Patent: May 29, 2018

(54) MODULAR ILLUMINATION AND SENSOR CHAMBER

(71) Applicant: Donald Channing Cooper, Boulder, CO (US)

(72) Inventor: Donald Channing Cooper, Boulder, CO (US)

( * ) Notice: Subject to any disclaimer, the term of this patent is extended or adjusted under 35 U.S.C. 154(b) by 0 days. days.

(21) Appl. No.: 14/936,966

(22) Filed: Nov. 10, 2015

(65) Prior Publication Data
US 2016/0131592 A1   May 12, 2016

Related U.S. Application Data

(60) Provisional application No. 62/077,890, filed on Nov. 10, 2014.

(51) Int. Cl.
*G01N 21/78* (2006.01)
*G06F 3/042* (2006.01)
*G06F 3/041* (2006.01)
*G01N 21/01* (2006.01)
*G01N 21/84* (2006.01)

(52) U.S. Cl.
CPC ......... *G01N 21/78* (2013.01); *G01N 21/8483* (2013.01); *G01N 2201/0221* (2013.01)

(58) Field of Classification Search
CPC .. G01N 21/78; G01N 21/8483; G06F 3/0425; G06F 3/0416
USPC ........................................................ 422/403
See application file for complete search history.

(56) References Cited

U.S. PATENT DOCUMENTS

| | | | | |
|---|---|---|---|---|
| 2011/0256024 | A1* | 10/2011 | Cole | A61B 5/0022 422/68.1 |
| 2012/0270600 | A1* | 10/2012 | Zelson | H04B 1/3888 455/556.1 |
| 2012/0282154 | A1* | 11/2012 | Slowey | G01N 21/8483 422/401 |
| 2014/0078594 | A1* | 3/2014 | Springer | G02B 7/16 359/672 |
| 2015/0002950 | A1* | 1/2015 | O'Neill | G02B 7/14 359/827 |

* cited by examiner

*Primary Examiner* — Jill Warden
*Assistant Examiner* — Jacqueline Brazin
(74) *Attorney, Agent, or Firm* — Kenneth Altshuler

(57) ABSTRACT

Embodiments described are generally directed to a test sample apparatus. The test sample apparatus generally comprises a holder base arranged that accommodates a tablet or cell phone. The apparatus has a hood that is placed over a portion of the tablets illuminating touchscreen such that the illuminating touchscreen provides light that can be collected by the hood. There is a chamber integrated with the hood adapted to accommodate a chemically activated test strip. The chemically activated test strip is illuminated when the hood collects light from the illuminating touchscreen. A lens in the hood interposed between the camera and the test strip enables the camera to focus on a portion of the chemically activated test strip when the hood is placed over the portion of the illuminating touchscreen.

20 Claims, 16 Drawing Sheets

MODULAR ILLUMINATION AND SENSOR CHAMBER

CROSS-REFERENCE TO RELATED APPLICATIONS

This application claims priority to and the benefit of U.S. Provisional Patent Application No. 62/077,890 entitled: MODULAR ILLUMINATION AND SENSOR CHAMBER, filed on Nov. 10, 2014, the entire disclosure of which is hereby incorporated by reference.

FIELD OF THE INVENTION

The present invention relates generally to test strip analysis using diffuse light from hand held devices, and more particularly to tools and methods used outside a laboratory for biological sampling.

BACKGROUND

Over recent years, biological sampling and testing in remote places is being seen as an important step in disease prevention and care. Today, most testing for disease or hazardous materials is done in a lab. These labs a located in cities or places that can accommodate first world equipment. Unfortunately, most of these labs are far from places where people are effected by hazardous materials and/or disease. Given advances in computing power of personal computers and hand held devices, laboratory services and test strip analysis may expand beyond central locations.

It is to improvements in test strip analysis using hand held devices that embodiments of the present invention are directed.

SUMMARY

Embodiments of the present invention are directed to test strip analysis using diffuse light from hand held devices with general accessibility to tools and methods used outside a laboratory for biological sampling.

One embodiment described herein contemplates a modular specimen illumination and positioning chamber system that attaches to mobile devices for the purposes of improving data acquisition resulting from imaging organic and nonorganic test specimens. The removable chamber is affixed directly over a front-facing camera and partially over an illuminated display screen in a consumer tablet or touchscreen cell phone, for example. The chamber gathers light from the illuminated display screen to provide indirect diffuse lighting to a specimen test strip. The color of the screen illumination region immediately under the chamber and the brightness of the screen may be adjusted programmatically using software algorithms to enhance specimen image acquisition. The chamber is capable of operating under a variety of mobile device orientations and is robust to physical disruption from dropping.

Embodiments can generally include modular specimen positioning with the use of an analysis chamber. One embodiment contemplates a mobile device at least partially contained in a base module having a protective case. The base module possessing an integrated removable lens holder. The base module adapted to accommodate a top stage module containing a window and removable specimen stage that fits on the base module in an adjustable manner in order to position the specimen in front of the front-facing camera. A portion of the base module chamber covers the display screen of the mobile device in an adjustable manner to gather light from the screen to optimally illuminate the chamber with indirect diffuse light. One embodiment contemplates the inside of the base module of the chamber being reflective to increase the luminance in the chamber. The walls of either the base or the stage module may be of varying opacities from translucent to opaque depending on the type of specimen and the type of imaging. The mobile device attached base module and lens holder may be moved from covering a portion of the display screen by sliding away from the display screen or pivoting on a hinge or axle from the display screen when loading the specimen, so that the camera can be used for non-magnified imaging or when the full touch screen is needed for user interaction.

The top stage module can be customized to accommodate the specimen. Embodiments contemplate the top stage module being removable and adjustable to accommodate X, Y and Z spatial positioning for securing a variety of specimen form factors and materials including wet and dry specimens for the purpose of image acquisition and analysis of the specimens.

Ancillary modules are envisioned to monitor specimen position in the chamber, changes in color and size of the specimen, environmental variables (such as temperature, humidity and wind or fluid velocity and volume), specimen source identification. Optional ancillary modules are further envisioned being capable of monitoring during sampling or imaging. Further modules may be employed for data storage security, such as for subsequent analysis.

DETAILED DESCRIPTION

Initially, the present disclosure is by way of example only, not by limitation. Thus, although the instrumentalities described herein are for the convenience of explanation, shown and described with respect to exemplary embodiments, it will be appreciated that the principles herein may be applied equally in other types of situations involving biological sampling consistent with spirit and scope of the present invention.

Figure 1:
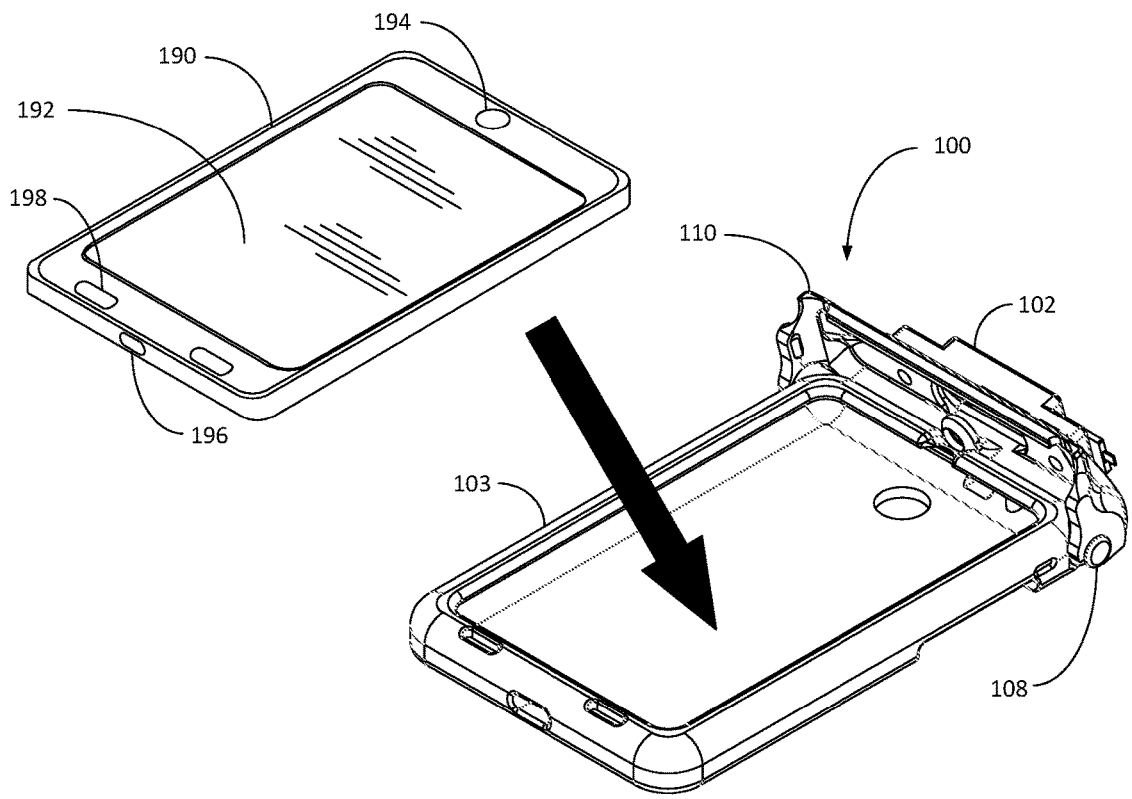
FIG. 1 illustratively depicts an embodiment of a handheld tablet or phone to be placed inside protective case embodiment consistent with embodiments of the present invention.

To illustrate an exemplary environment in which preferred embodiments of the present invention can be practiced, FIG. 1 depicts an embodiment of a cell phone/tablet 190 that is to be placed inside of a protective case 100, or more specifically the protective case base 103. Certain embodiments contemplate the protective case base 103 essentially conforming to all sides of the cell phone/tablet 190 while other embodiments contemplate the protective case base conforming to only a portion of the cell phone/tablet 190. The cell phone 190 is simply an embodiment of a tablet or other handheld electronic device that could likewise be used within the scope and spirit of the present invention. As illustratively shown, the cell phone/tablet 190 possesses a screen 192, preferably a touchscreen, a camera 194, speakers 198, and power inlet 196, etc. The protective case 100 possesses a hood 110 that is adapted to be pivoted to over a portion of the cell phone/tablet 190. The arrow indicates where the cell phone/tablet 190 is placed inside of the protective case 100.

Consumer electronic mobile devices, such as tablets or phones 190, capable of wireless (Wi-Fi or cellular network) data transmission have computer processing capability and user interface operating systems. Most have a fixed-focal-length camera 194 that are positioned above the illuminated display screen 192, called a front-facing camera. The display screens 192 are typically touch screens that enable users to interact with the operating system via touching the screen when 92. The screens are color displays consisting of Red, Green Blue, Cyan or Magenta colored pixels capable producing any color combination. In addition, the illumination of the screen display can be adjusted in brightness from 0 to 100% of the device output.

Figure 2A:
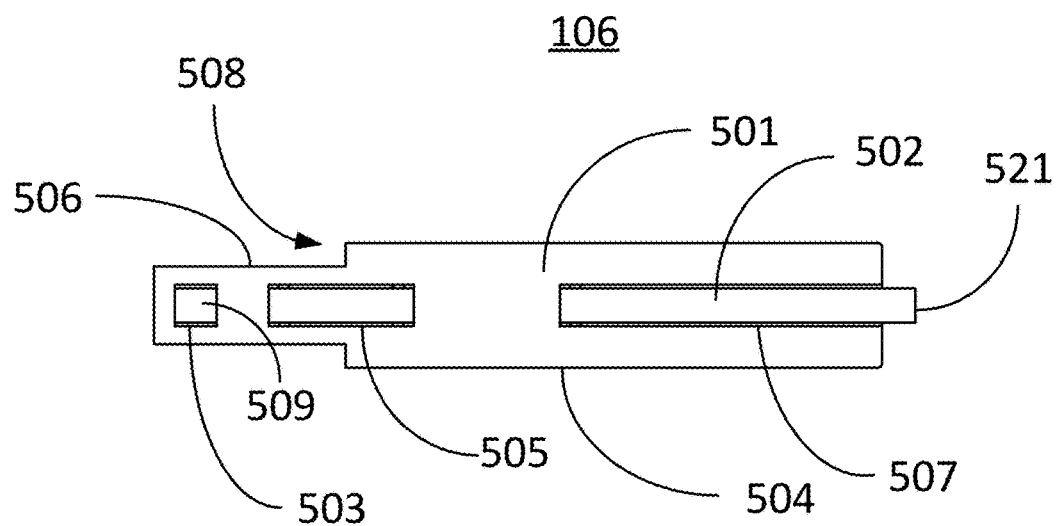
FIGS. 2A-2C depicts illustrations of a strip holder with a test strip consistent with embodiments of the present invention.
Figure 2B:
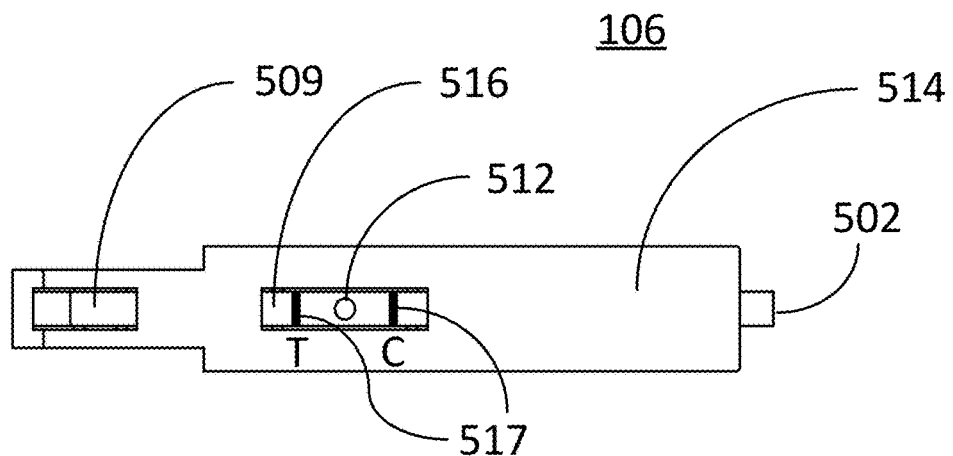

With reference to FIGS. 2A and 2B, depicted therein are illustrations of a customized strip holder 106 accommodating a test strip 502. FIG. 2A illustratively shows the top surface 501 of the customized strip holder 106 and FIG. 2B illustratively shows the bottom surface 514 of the customized strip holder 106. The present test strip 502 embodiment is a lateral flow test strip 502. Certain embodiments contemplate the test strip 502 being a chemically activated test strip, that is when molecules of a specific substance are migrated through the test strip 502 they react with Test and Control lines to indicate the presence of the molecules. From the perspective of the top surface 501, the lateral flow test strip 502 is exposed in three windows 503, 505, and 507. The test strip 502 comprises three elements of interest: 1) the test pad 509, which is an absorbent material, 2) test and control lines 517, which are used to reveal the outcome of a biological test, and 3) the holding portion 521. When in operation, the absorbent pad 509 is dipped into a test solution, such as a biological solution (e.g., blood, saliva, sweat or any other biological fluid to be extracted from an animal or extracted from grain or plant material with a solvent). The test solution absorbed by the absorbent pad 509 migrates to the testing control region 505 along with antibodies or antigens previously embedded in the test strip 502. Certain embodiments contemplate a test strip that is constructed with nitrocellulose material membrane between 503 and 505 that easily carries the naturally aqueous solution by way of capillary action. The aqueous solution carries the antibodies along the test strip 502 to the imaging window 516, which reveals the test area that provides a visual signal on stripes/lines "T" (Test) and "C" (Control) 517 within imaging window 516. The center of the imaging window 516 is illustratively shown by the circle 512. The center of the imaging window referenced by the circle 512 is the location where the cell phone/tablet 190 camera 194 centers on the test strip 502 to evaluate the stripes "T" and "C" 517.

The "T" and "C" stripes 517 are not originally visible (or present) until the test solution is absorbed and transferred to the testing control region 505. More specifically, the antibodies are conjugated to some tag, such as colloidal gold, wherein the antibodies bind to the binding site "T" on the membrane 502. The lines "T" and "C" 517 become gradually darker depending on (directly related to) the particular analyte that is being tested. The control line "C" is a standard line reference where the antibodies conjugate. The test line "T" has either a) a competitive interaction with the test analyte and the binding site, "T", such that when there is more analyte the test line "T" gets darker or b) it is configured in a sandwich assay where the signal becomes darker with an increasing amount of analyte. A rapid diagnostic test strip, such as a pregnancy test strip, is an example of a standard test strip 502. Neogen Corporation of Lansing, Mich. can provide a test strip to test for mycotoxins, which can be aptly used, for example, in the present embodiment. In one example, a ratio metric and can be used to quantify the intensity of the test signal "T" relative the control signal "C", which can be calibrated to a standard curve having known signal intensities, to determine the concentration of a particular analyte in solution.

With continued reference to the structure of customized strip holder 106, the is a shoulder 508 that acts as a "stop" to position the customized holder 106 and test strip 502 appropriately in the top chamber 102 so that the test lines "T" and "C" 517 are centered over the tablet camera 194.

Figure 2C:
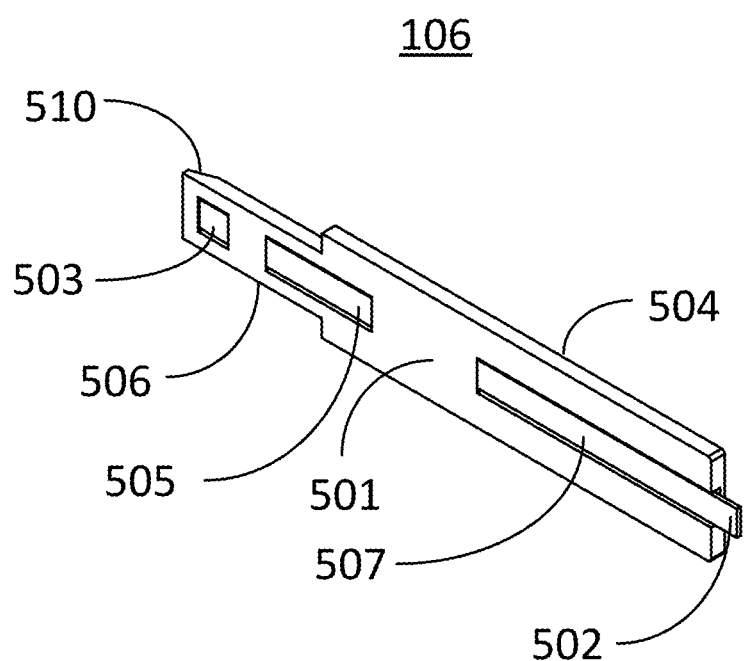

FIG. 2C illustratively depicts a perspective drawing of the customized strip holder 106 with the top surface 501 revealed. Note that the customized strip holder 106 possesses a leading ramp 510 that facilitates an easy insertion of the customized strip holder 106 into the top chamber 102. The customized strip holder 106 and test strip 502 allow for a user to start developing the test strip 502 while holding the customized strip holder 106 prior to insertion into the top chamber 102.

Figure 3A:
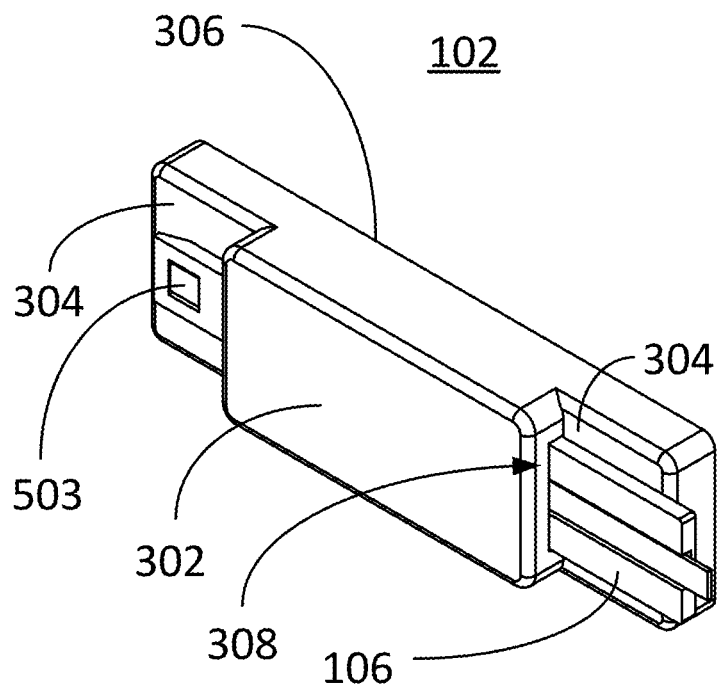
FIGS. 3A-3D illustratively depict an embodiment of a top chamber consistent with embodiments of the present invention.
Figure 3B:
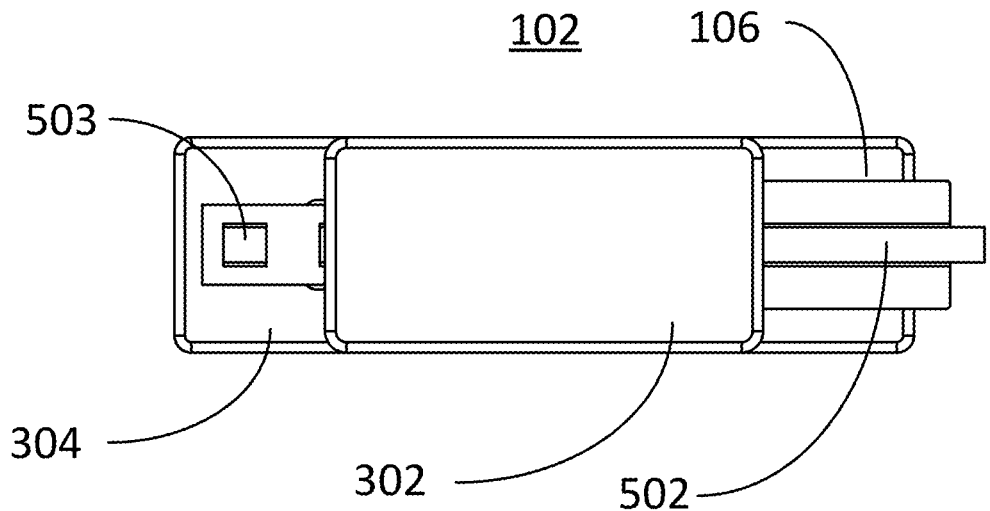
Figure 3C:
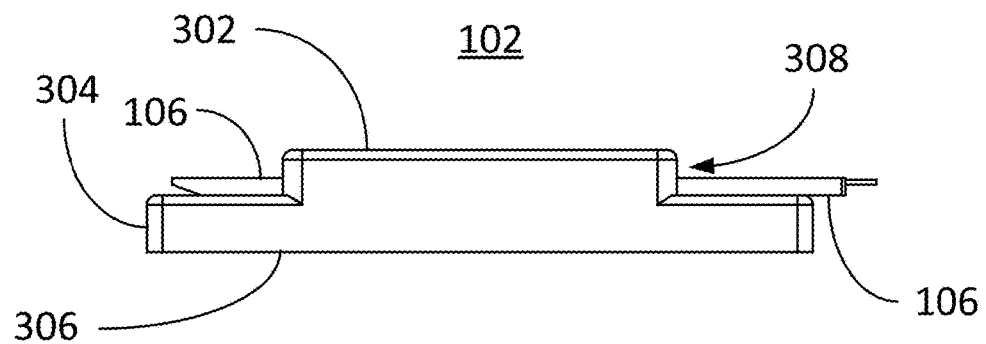

FIGS. 3A-3D illustratively depict an embodiment of a top chamber 102 adapted to affix to the hood 110, the top chamber 102 consistent with embodiments of the present invention. Embodiments contemplate the top chamber 102 accommodating any number of standard test strips and certain embodiments contemplate other standards strip holders, that may be different from the strip holder 106 depicted in FIG. 2A, for example. FIG. 3A depicts a perspective view of the top chamber 102 with the customized strip holder 106 accommodating a test strip 502. The top chamber 102 position in view of the top surface 302 depicts a pair of steps 304 that provides access to the front window 503 and easy access to the insertion location 308. Other embodiments of the top chamber 102 envision optional geometries to provide access to the front window 503 and insertion location 308, consistent with embodiments of the present invention. The customized strip holder 106 is disposed in the top chamber 102 by way of a strip holder insertion location (opening) 308. FIG. 3B depicts the top view of the top chamber 102. Again, as illustratively depicted, the top surface 302 steps down into a lower surface 304 whereby the customized strip holder 106 provides visibility to the front window 503 and access to insert and remove the customized strip holder 106 at the insertion location 308. FIG. 3C illustratively depicts a side view of the top chamber 102. As shown, the customized strip holder 106 is held in place in the top chamber 102. The customized strip holder 106 is inserted through the insertion location 308 from the right side of the top chamber 102 to the left side of the top chamber 102. Also shown, is the bottom surface 306 of the top chamber 102, which is affixed to the hood 110.

Figure 3D:
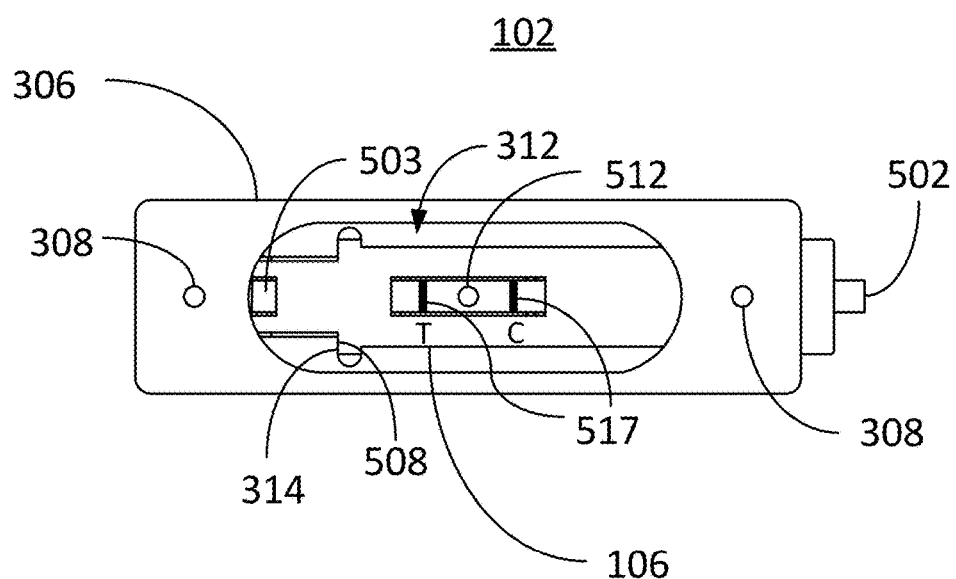

With reference to FIG. 3D, shown therein is the bottom surface 306 of the top chamber 102 consistent with embodiments of the present invention. The bottom surface 306 of the top chamber 102 possesses a pair of holes 308 (potentially screw holes) that can affix the top chamber 102 to the hood 110. Embodiments contemplate other elements of fixing the top chamber 102 to the hood 110, such as magnets, screws, pins, adhesive, latches, etc. As shown here, the customized strip holder 106 is exposed through an opening 312 extending through the bottom surface 306 of the top chamber 102. In this way, the test strip 502 is exposed to the camera 194 in the tablet 190 via the opening 312 in order to be analyzed by the camera 194. Also, shown is the shoulder 508 butting up against the mating surface 314 in the top chamber 102 to position the center of the imaging window 516 and the test strip 502 (the circle 512) with the focal point of the camera 194. Embodiments contemplate the opening 512 and the testing control region 505 positioned in a different location to be aligned with one or more cameras if located on the front of a tablet 190 in a different locations, such as on the side or not in the midpoint between the two sides of the tablet 190.

Figure 4A:
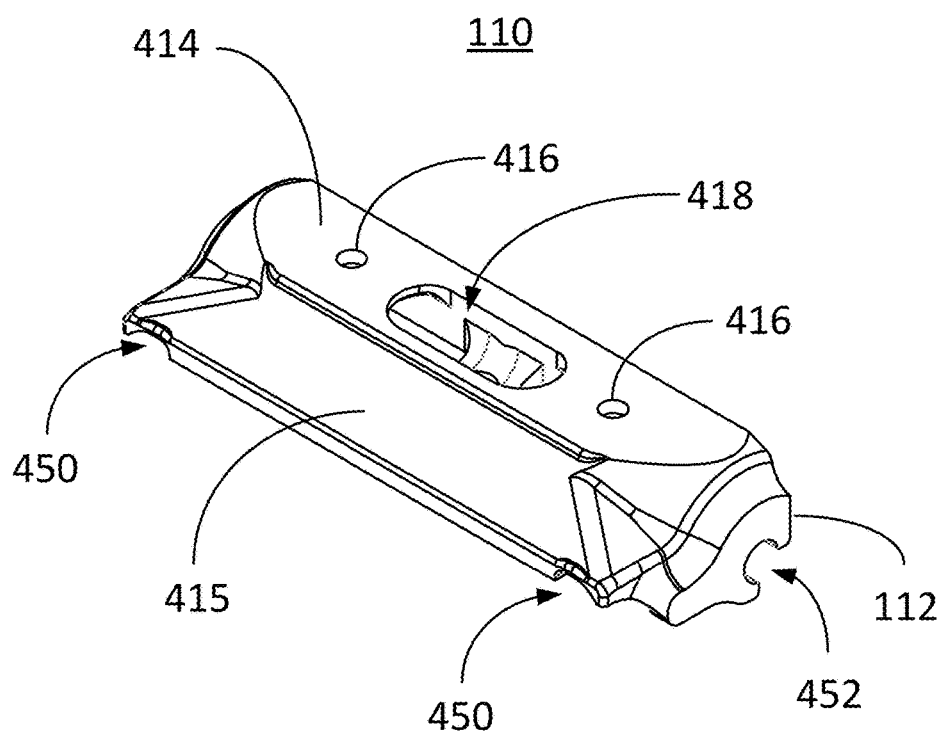
FIGS. 4A-4C, depict illustrations of a flip hood embodiment is depicted consistent with embodiments of the present invention.

FIG. 4A depicts a perspective illustration of a flip hood embodiment consistent with embodiments of the present invention. As shown, the flip hood 110 possesses a top surface 414 without the top chamber 102 mounted thereon. There are two holes 416 that align with the two holes 308 from the top chamber 102. Accordingly, the top chamber 102 can be affixed to the flip hood 110 via magnets, screws, adhesive, pins, latches, and the like without departing from the scope and spirit of the present invention. The top surface 414 of the flip hood 110 possesses a flip hood opening 418 through which light from the screen 192 can illuminate the test strip 502 and the camera 194 can freely image the illuminated test strip 502 via the opening 312 in the top chamber 102. The flip hood 110 possesses two hinge points 452 on the sides 112 that cooperate with two posts 108 protruding from the protective case base 103. The two hinge points 452 enable the flip hood 110 to rotate away from the screen 192 so that a user of the tablet 190 can enter in data or use the screen 192 without obstruction of the hood covering part of the screen 192. Furthermore, rotating the flip hood 110 away from the screen 192 facilitates disposing or removing the tablet 190 from the protective case base 130. The flip hood 110 further possesses a flip hood cover 415 that slopes down from the top surface 414 and is adapted to collect light emitted by the screen 192 from the tablet 190. Also depicted, are two flip hood notches 450 that mate with protrusions 160 on the protective case base 103 to hold the flip hood 110 in a down position when examining a test strip 502. Optional embodiments contemplate the flip hood 110 being held down in a held or latched in position with the help of magnets or two rubber foot protuberances on the back, bottom surface of the flip hood which extend beyond the case back surface to allow the device's weight to rotate the hood to keep it closed, for example prior to illuminating the sample and taking a picture. Other latching embodiments can include locking features, snapping features, Velcro, and the like within the scope and spirit of the present invention.

Figure 4B:
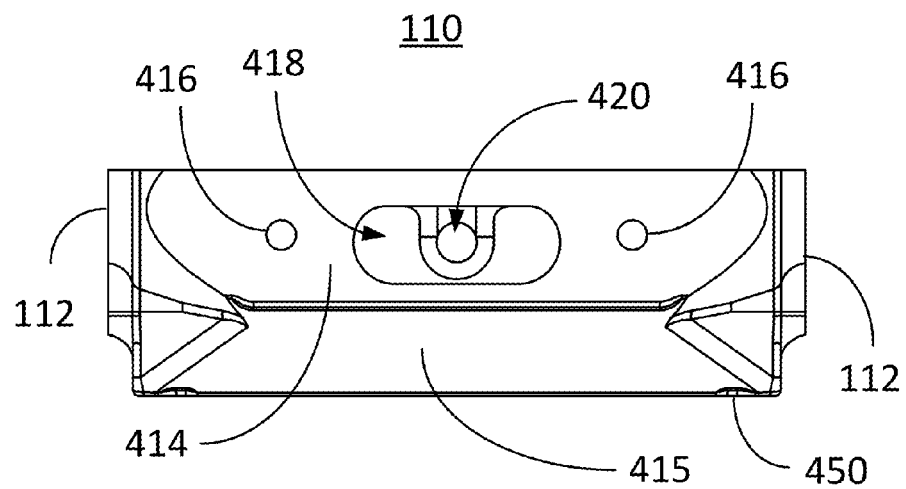

FIG. 4B depicts a top view of the flip hood 110 consistent with embodiments of the present invention. The two holes 416 are located in the top surface 414 as previously discussed. The flip hood opening 418 reveals a lens 420 that is located directly above the camera 194 associated with the tablet 190 to bring the center point 512 of the imaging window 516 into focus. The lens 420 is preferably a convex lens, but can be a plurality of different kinds of lenses to produce different levels of magnification and focus within the scope and spirit of the present invention. Some lenses 420 may have different focal lengths and magnifications and may be spherical, semispherical, planar, concave or convex in shape and may be made from glass, epoxy, polyacrylamide, plastic, liquid or other translucent or tinted materials. The lens 420 may be disposable convex planar and made of aqueous liquid containing translucent or tinted polyacrylamide to provide magnification at different powers from 2× to 40× depending on the size of the semispherical disposable lens and may be tinted to serve as a filter to allow specific wavelengths of light to pass 420. For reference, the flip hood notches 450 are shown on the flip hood cover 415.

Figure 4C:
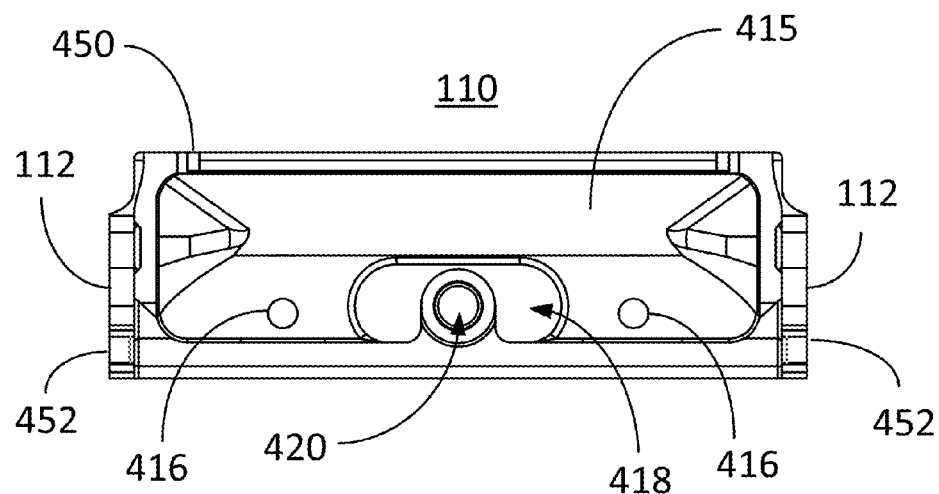

FIG. 4C depicts an underneath view of the flip hood 110 consistent with embodiments of the present invention. As is illustrative of shown, the flip hood opening 418 shows the lens 420 located in the middle of the flip hood opening 418. Other embodiments contemplate the lens 420 capable of being adjusted to the left or to the right in the flip hood opening 418 to adjust in alignment with the camera 194 in the tablet 190. Optionally, other embodiments contemplate the lens 420 capable of being removed altogether. From the underneath perspective, the flip hood 110 shows the attachment holes 416, the sides 112, the two hinge points 452, the two flip hood notches 450, and the flip hood cover 415. As discussed earlier, the flip hood cover 415 collects light emitted from the screen 192 of the tablet 190 to expose the test strip through the flip hood opening 418.

Figure 5A:
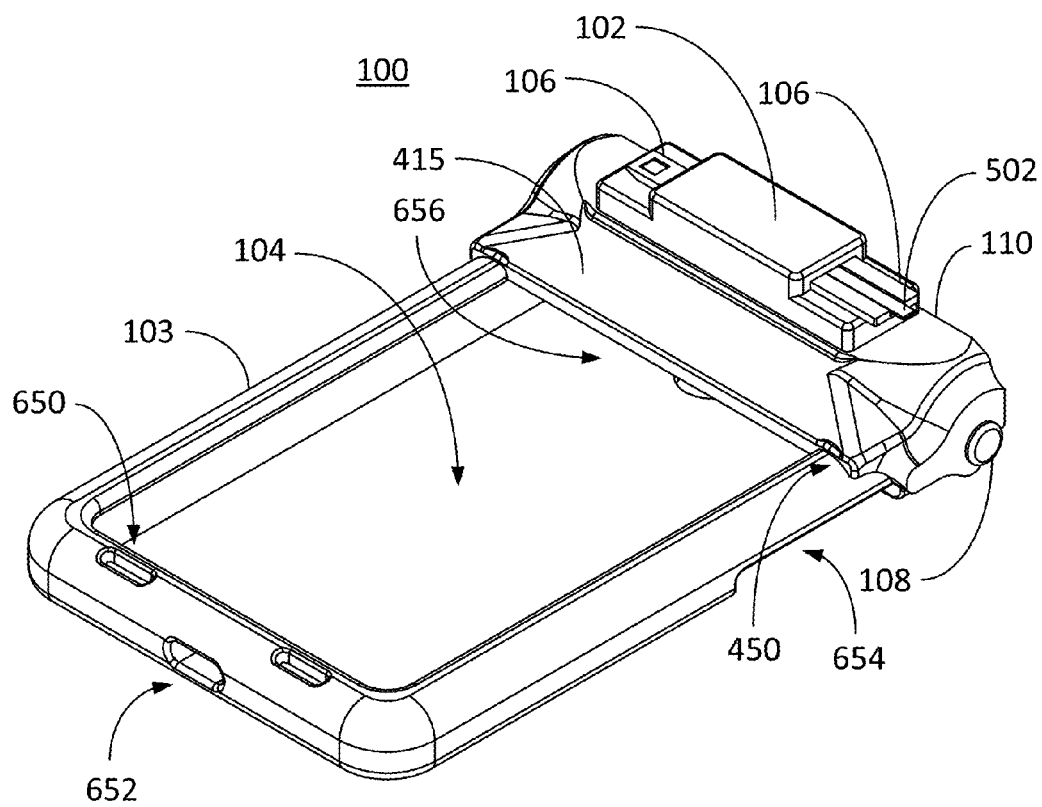
FIGS. 5A-5B illustratively depicts an embodiment of the protective case in more detail in accordance with embodiments of the present invention.

FIG. 5A illustratively depicts an embodiment of the protective case 100 in more detail in accordance with embodiments of the present invention. In the present drawing, there is no tablet 190 present. In the present view, the flip hood 110 is latched down in the closed position, which is spaced apart from where the screen 192 of the tablet 190 would reside if present. The flip hood 110 (a light collection chamber) is spaced a distance apart 656 from the screen 192 in order to a) collect light from the screen 192 and b) provide adequate distance between the customized strip holder 106, and more specifically the test strip 502. Preferably, the flip hood 110 is spaced at distance apart 656 from the screen 192 between 1 mm and 6 mm, though other embodiments envision different dimensions. The protective case 100 possesses a protective case base 103, which in certain embodiments contemplate being a rubber bumper or some other kind of bumper that allows for deflection to protect the tablet 190. The protective case base 103, in one embodiment, wraps around the tablet 190 holding it snugly in place so that the tablet 190 is constrained and is protected. The protective case 100 can further possess speaker holes 650 and a hole for power 652. One skilled in the art will appreciate that the speaker holes 650 and the power hole 652 may be located in different places in the protective case base 103 in order to accommodate those structures in the tablet 190. Other cutaways, such as the cutaway 654 are envisioned to support other buttons on the tablet 190. Embodiments of the elements found in the protective case 100, though not limited by the following material options, may be made from rubber, silicone, wood, metal, glass, plastic, polyurethane, vinyl, PLA, paper, ABS and other epoxy-based or malleable materials, just to provide some examples.

Figure 5B:
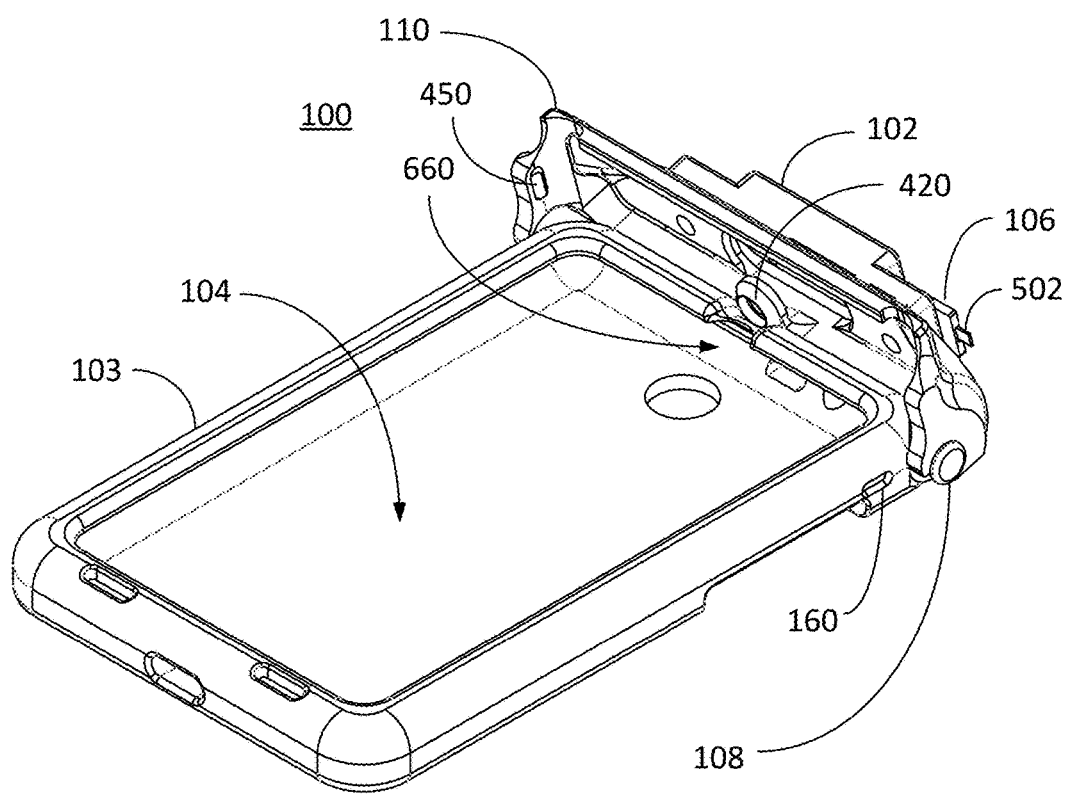

FIG. 5B illustratively depicts an embodiment of the protective case 100 with the flip hood 110 pivoted in an open position to allow for insertion of a tablet 190 or facilitate the use of a touchscreen 192 associated with the tablet 190. In the present embodiment, the side of the protective case base 103 possesses protrusions 160 that mate with the flip hood notches 450 to hold (lock) the flip hood 110 in a down position (in place) when examining a test strip 502. The protective case 100 also possesses a lens cutaway 660 in order to accommodate the lens 420 (and lens structure) when the flip hood 110 is moved between an opening closed position.

Certain embodiments contemplate the flip hood 110 to be further capable of gathering light from the display screen 192 by its physical placement over the screen 192 and redirecting the light to illuminate the specimen 502. This may be aided by the use of highly reflective coating of the interior walls of the base module or by placing mirrors in the chamber 102 and/or the flip hood 110 to redirect light from the display screen to the specimen 502 or from the specimen 502 to the camera lens 194. The display screen illumination may be adjusted to increase or decrease the luminance or wavelength color of light within the chamber 102 to enhance the illumination of the test strip 502 for image acquisition (perhaps ultraviolet or infrared). Certain embodiments contemplate using various wavelengths of light generated by the touchscreen 192, such as ultraviolet, to cause reaction or develop the chemically activated test strip 502 when introduced to a test sample Some embodiments contemplate a filter, prism or pinhole integrated into the lens holder module or, optionally, exist as a separate module for allowing certain wavelengths of light to pass from the specimen to the camera lens. Some embodiments contemplate the walls of the chamber 102 and or flip hood 110 being translucent to allow trans illumination or oblique lighting of the test strip 502 or it may be opaque to shield from ambient light sources depending on the type of test strip 502 and use case.

It is contemplated that the display screen 192 may be adjusted programmatically to increase or decrease the light emitted from it in order to modulate the lighting of the specimen/test strip 502 in the chamber 102. Other embodiments contemplate the display screen 192 being adjustable, to adjust the color of light emanating from the screen used to illuminate the specimen/test strip 502. Certain other embodiments contemplate the tablet or cell phone 190 connecting to a specimen imaging trigger module that may be powered by the tablet or phone 190 via a power port 196, or audio headphone port and the like, to provide an electrical contact with the specimen material of the test strip 502 sensing voltage signals indicating initiation or termination of imaging. This can be used to trigger the camera 194 and/or provide other actions of the tablet or phone 190, such as initiation of imaging, timing, illumination, or analysis of the specimen via software programs/modules. The software applications stored in non-transitory memory in the tablet 190, or elsewhere, can be accessed by the computer system processors in the tablet or elsewhere.

Certain other embodiments contemplate the flip hood 110 or elements associated with the flip hood 110 being adjustable in order to provide precise fixed positioning of the test sample 502 over the camera 194 and illumination screen 192. Certain adjustable mechanism such as finger screws, for example, could adjust the flip hood 110 and associated elements in the X, Y, Z directions.

Figure 6A:
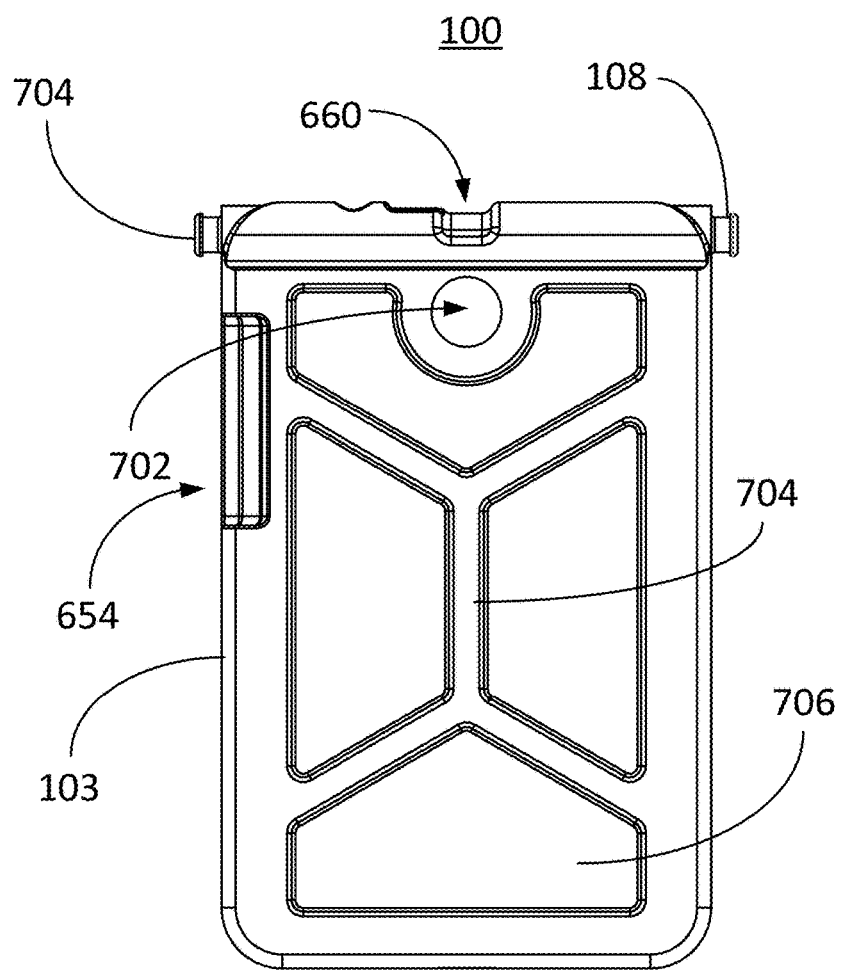
FIG. 6A-6C illustratively depict an embodiment of the protective case consistent with embodiments of the present invention.

FIG. 6A illustratively depicts an embodiment of the protective case 100 as viewed from the bottom. The protective case base 103 possesses a protective case bottom 706 that in this configuration possesses a raised rubber grip 704. The cutaway 654 as described in conjunction with FIG. 5A is shown here providing access to buttons on the tablet 190. Also depicted, is a protective case base reverse side camera opening 702 that provides access to a camera (not shown) on the reverse side of the tablet 190. Also shown, is the lens cutaway 660 and the two posts 108 protruding from the protective case base 103. In this embodiment, each post 108 possesses a rubber ear 704 that is adapted to deflect and retain the flip hood 110 when cooperating with the hinge points 452 on the sides 112. Other embodiments contemplate the posts 108 extending far enough from the protective case base 103 to facilitate a strap (not shown) looping around the posts 108.

Figure 6B:
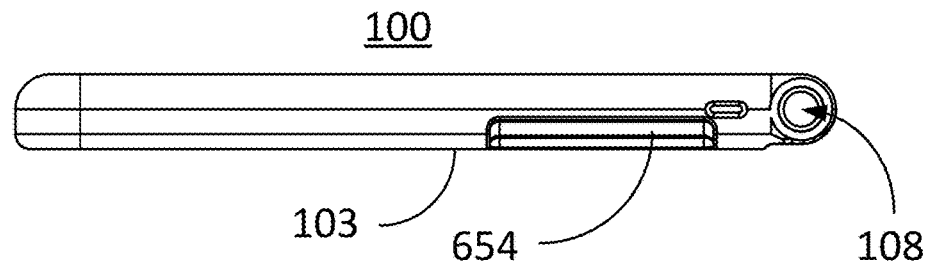

FIG. 6B illustratively depicts the embodiment of the protective case 100 as viewed from the side. As depicted, the protective case base 103 is just thick enough to accommodate the tablet 190, such that the tablet 190 is essentially contained therein and protected. For reference, note the cutaway 654 as described in conjunction with FIG. 5A and one of the posts 108.

Figure 6C:
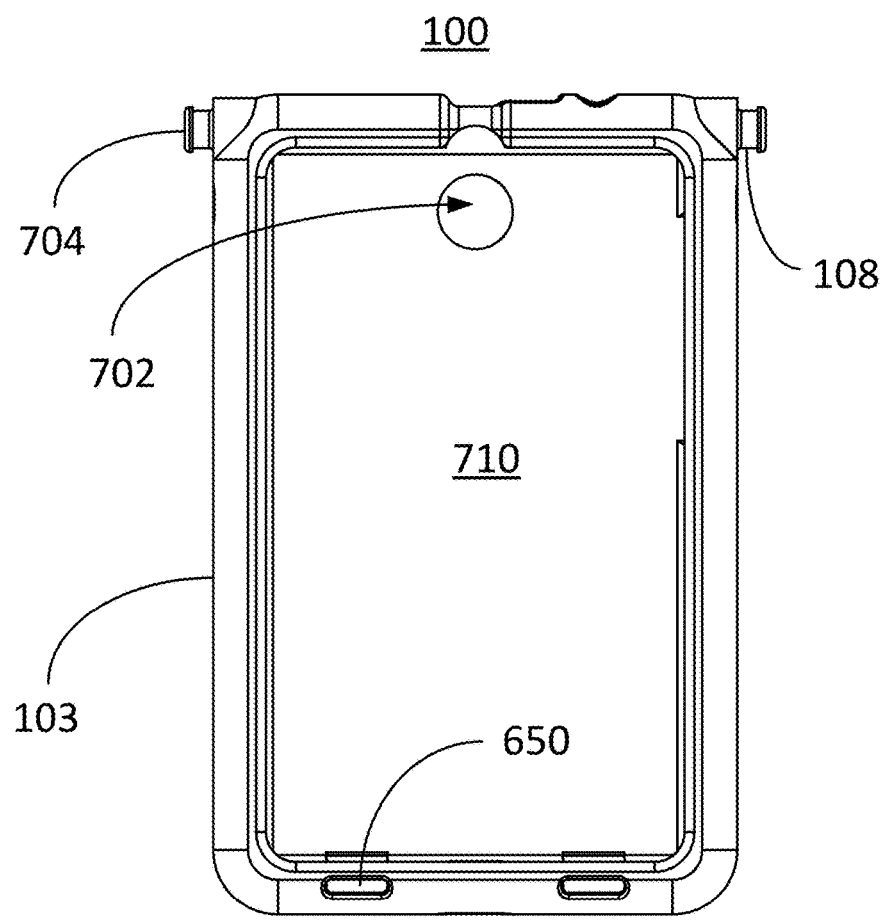

FIG. 6C illustratively depicts the embodiment of the protective case 100 as viewed from the top down. For reference, the protective case base reverse side camera opening 702 is shown penetrating the interior protective case base portion 710. Also, the two posts 108 are shown protruding from the protective case base 103 along with the rubber ears 704 on each post's 108 distal end.

The figures described above are illustrative examples of a protective case 100 and system used with consumer-based mobile electronics for quantitative imaging acquisition and analysis that are solutions to deficiencies in the present state of the art. One of the problems with the present state of the art when evaluating test strips 502 with a light source, typically an LED (Light Emitting Diode) light source, is the variability and quality of the LED "Flash" luminance intensity between devices providing the light. The LED "flash" operates in a binary on or off mode. There is no software programmatic method of adjusting the output luminance in a continuous manner. In addition, the LED is a high intensity point-source of light, and when imaging objects within a few centimeters of the camera lens and LED light-source artifacts, such as reflection, glare and shadows may be introduced. These artifacts make it difficult to perform quantitative high magnification (>2 X) optical imaging of biological samples or "wet/moist" objects on highly reflective surfaces, such as aqueous-sample-treated white nitrocellulose immunotests or glass microscope slides. In addition to the artifacts associated with LED illumination coupled with use of the rear-facing camera (the camera opposite to the touchscreen display 192), the autofocus, ISO, color correction and automatic white balance adjustments that are built in features of many mobile device hardware operating systems (e.g. Windows, Android and iOS) are not uniform in their performance especially for high magnification imaging, which results in variability in the images and makes it difficult for quantification with reliability between devices.

Specimen sampling and analysis of biological fluids and tissues are discovered, via developing this device, to be prone to errors derived from improper sampling procedures, cross-contamination, errors in subject or sample identification, inconsistent methods across individuals or test devices, improper calibration to standards, measurement errors, expired reagents and supplies, improper handling and cold chain management of samples or reagents, lost or corrupted data, fragile test equipment, and intentional data falsification.

Embodiments contemplate the protective case 100 and flip hood 110 (of FIG. 1) providing a cross-platform rugged modular specimen imaging and analysis chamber 102 that are able to work with a variety of mobile devices in order to eliminate variability associated with specimen positioning, illumination, temporal changes in the color or shape of the specimen during testing, specimen source identification and tracking, and environmental fluctuations during testing, and high-risk data storage.

The modular illumination chamber 102 uses a front-facing camera 194 and the illuminated display 192 as an indirect and diffuse light-source from a tablet or cell phone 190. There are several advantages of using the front-facing camera 194 positioned directly above the illuminated display screen 192. Typically, a tablet or cell phone 190 has a fixed focal length camera so there is no automatic autofocus mechanism as a source of variability. In addition, the display luminance and color wavelength on most displays 192 of mobile devices 190 is continuously adjustable from 0 to 100% brightness and from 380 nm (Blue) to 650 nm (Red) wavelengths. Indirect lighting from the display screen 192 into the hood 110 and the illumination chamber 102 provides diffuse, polarized LCD illumination of the specimen 502, which eliminates glare and artifacts associated with point sources of light and with magnified imaging of objects with complex shape (e.g. conical tubes) and/or reflective or wet surfaces.

The ports of audio or micro USB inputs in tablets or cell phones 190 and may be used to collect data before, during or after image acquisition in order to improve specimen positioning, identification, handling, sampling and data storage.

Certain embodiments contemplate instructions being interpreted by the tablet or cell phone 190 via the test sample, such as, information embedded in barcodes, text, shapes, colors, QR codes, or any other reliable identifiable features associated with the specimen for purposes of triggering image acquisition, color and intensity of the illumination screen 192, storage of information to the tablet, real-time digital image analysis, object recognition algorithms, feature detection, background subtraction, filtering methods, contrast enhancements, pattern recognition and other computer vision techniques to assess specimens spatial, spectral and temporal imaging characteristics, for example. Real-time image acquisition and analysis can benefit from the combined use of the illumination specimen positioning modules, display screen illumination and color determination, mobile device user input and software algorithms running on the mobile device to perform/execute the computational algorithms.

With respect to the test lines "T" and "C" 517, certain embodiments contemplate analyzing test lines "T" and "C" 517 (region of interest) via a data visualization module, such as a software module, that translates the predefined rectangular region of interest of the test strip 502 into a simulated representation that is displayed on the screen. This simulated representation is referred to as an "image schematic" showing the relative RGB pixel density of one or more test regions normalized to one or more control regions of the same size against a constant color background. Determining the relative pixel density of the "T" and "C" 517 region is called "mobile image ratiometry" and it is applied to the quantitative image analysis of lateral flow immunodiagnostic tests. The image schematic enables the agent (human, robot) imaging the specimen to compare the mobile device/tablet simulation of the test strip 502 to visual inspection to assure that the algorithms are functioning properly and the test strip 502 is oriented in the correct position. The image schematic information may also be transformed into an audio, tactile, or voltage signal to represent the relative Test/Control ratio. The digital image schematic contains all the information needed for ratiometric analysis yet its file size is a small fraction of the original specimen image region of interest. Certain benefits include greater storage capacity, faster data transmission to central or distributed servers and reduces processor activity.

Human perceptual validation of the image schematic simulated representation of the relative ratio of the "T" and "C" 517 regions of an image may be accomplished by showing individuals (humans/onlookers) a test strip 502 or its image on the mobile device or computer display, then allowing them to compare and score it to the image schematic along with other image schematics that deviate from the calculated ratios. Embodiments contemplate individuals being shown two or more images on a screen and asked to choose (rate) between two images according to the Test/Control "T" and "C" region ratio. Using this "game-like" method the Test/Control ratio is not measured absolutely; it is inferred from the collective binary (higher or lower) judgments of the human raters. The rank order of any given image depends on the ratings of the other images and is described mathematically by the Elo formula (see below) for ranking two opponents in a competitor vs competitor match. For image A the formula is:

$$E_a = \frac{1}{1 + 10^{\frac{R_b - R_a}{400}}}$$

For image B the formula is:

$$E_b = \frac{1}{1 + 10^{\frac{R_a - R_b}{400}}}$$

$E_x$ is the expected probability that X will win the match, i.e. $E_a + E_b = 1$.
$R_x$ is the rating of X, which changes after every match, according to the formula $(R_x)_n = (R_x)_{n-1} + 32 (W - E_x)$ where W=1 if X wins and W=0 if X loses.
Every image starts with an $R_x = 1400$.

In this example, an image score is generally not obtained until it has been matched to at least 10% of the total pool of images that it could be matched against if the image pool size is fixed; otherwise a score is obtained after 100 (or some substantial number) randomly selected from match pairings of an arbitrary sized pool. The results of the scored images may then be used to quantify the images by placing into the image rating pool known or predetermined image ratios as standards. The standards may be derived from Test/Control ratios that have been measured using the modular specimen imaging chamber described above attached to a mobile device or may be simulated by a computer or mobile device as image schematics. This method of human perceptual validation of images may be used in the diagnostics field for quantifying colorimetric or immunobased lateral flow tests that have Test and Control regions.

The composite ratio for ratiometric measurement of Test and Control regions to quantify image pixel density. The composite ratio can be calculated as the weighted average of the test and control regions peak pixel density and the test and control regions areas under the curve. The formula is as follows $(T_{(peak)}/C_{(peak)})/2+(C_{(area)}/C_{(area)})/2=$Composite ratio at 50/50 Peak and Area. Note that other weights can be assigned by changing the denominator. The use of different weighting schemes may be used depending on the type of specimen analysis that is needed.

The composite ratio reduces the image-to-image variability arising from test or control regions of interest that are not homogenous in the pixel density. Subregions of the test or control regions of interest that have very high peaks are seen as dark bands or spot within the regions of interest and these high peaks can produce error and variability when measuring between specimens. To reduce the possibility for error and variability the baseline-subtracted area under the curve within the test and control regions is measured. A curve (created by nonlinear regression) is a series of connected XY points. The software algorithms running on the mobile device use the following trapezoidal integration formula, $\Delta X*(Y1+Y2)/2$ repeatedly for each adjacent pair of points defining the curve. The area is the result of this calculation and establishes the basis for the $T_{(area)}/C_{(area)}$ ratio. To further reduce image-to-image variability and enhance sensitivity the composite ratio is calculated for three separate images and the results are averaged to produce the final composite ratio.

Embodiments for baseline subtraction method for determining the composite ratio for quantitative ratiometric image analysis contemplated can be used to remove or reduce noise and other artifacts from test and control regions-of-interest of specimen images. The defined rectangular region of interest is determined by the placement of the specimen in the illumination chamber top stage module that is positioned in front of the camera. Embodiments contemplate the RGB values from 0 to 255 measured by the mobile device camera hardware and software for each pixel in the vertical (Y dimension) or horizontal (X dimension). The two-dimensional planar region of interest can then be transformed into a one-dimensional line with a horizontal or vertical orientation. This dimensional transformation is termed a line profile and it establishes the basis for all subsequent quantitative measurements of the region of interest. The first point of the horizontal or vertical line profile is used to establish the starting baseline. The middle point of the line profile is used as a second point to establish the baseline. The last point in the line profile is used as the third point to establish the baseline. A line curve is fit between the first and second points and again between the second and third points. These two curve fits are merged into one curve fit, which is then subtracted from the region of interest line profile. This procedure establishes the baseline pixel as zero and it de-trends the line profile by removing background shadows or noise. The resultant baseline subtracted line profile is the dataset that is used for peak and area calculations and provides the information needed to create the composite ratio and the image schematic.

An alternative method to remove the initial baseline value from the line profile is envisioned to be to establish the line profile as described above and then differentiate the line by calculating the point-to-point slope change to produce a slope line profile, then integrating the slope line profile using point-to-point trapezoidal integration ($\Delta X*(Y1+Y2)/2$). The original shape of the line profile is re-established with the baseline offset removed. This technique removes the initial baseline, but generally will not remove background noise or shadows across the line profile.

An alternative method to remove the initial baseline value from the line profile envisioned to be to calculate the central tendency (average, median or mode) of a range of values in the beginning of the line profile before the signal begins and subtract the average, median or mode value from the entire line profile and determine which of the three produces the largest signal-to-noise ratio or most reliable result across several images. Under most circumstances when the baseline noise is normally distributed the average is approaching optimal. Under conditions where there are large transient artifacts in the baseline segment of the line profile the median would yield reasonable results.

Figure 7:
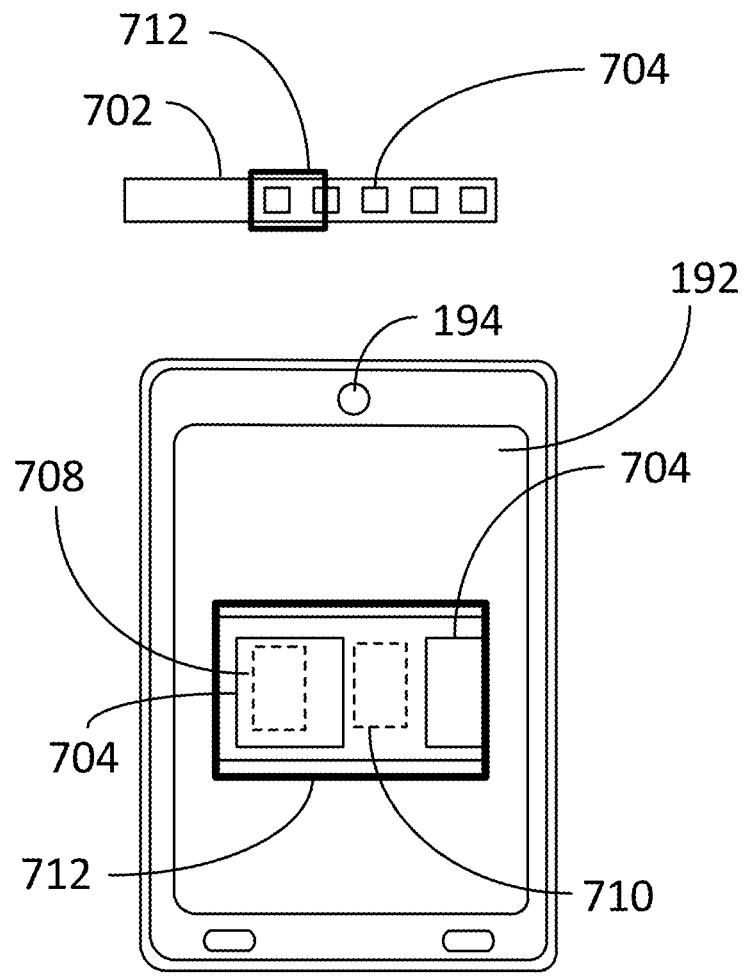
FIG. 7 illustratively depicts a test strip embodiment with an image schematic of a region of interest within an image displayed on a screen consistent with embodiments of the present invention.

An example where certain embodiments of the present invention can be commercially practiced is illustratively shown in FIG. 7. FIG. 7 shows the colorimetric quantification of a colorimetric test with five colored changing pads 704. The test strip 702 is placed in the illumination chamber 102, illuminated with the display screen 192, and imaged via the front facing camera 194 (the image is the darkened rectangle 712 indicating the boundary of the picture frame). The resulting image 712 is shown on the display screen 192. The region of interest is defined by the person operating the mobile phone/tablet 190 by drawing a single box around the signal 708 and background 710 of the sample image 712. The signal box 708 and background box 710 are equal sized boxes. The average Red, Green, Blue (RGB) color channel values are determined for the two boxes 708 and 710 and the ratio of the signal/background is compared to known standards for each colored pad of interest.

Certain embodiments contemplate the data visualization module being a software program running on the tablet/phone 190 that translates a predefined rectangular region of interest, which positions itself over the picture 712 (box 708 and 710, for example) of the test strip 702 that is displayed on the display screen 192. The region of interest is determined by the correct positioning of the test strip/specimen 702 within the image illumination chamber 102 and over the front facing camera 194.

Figure 8:
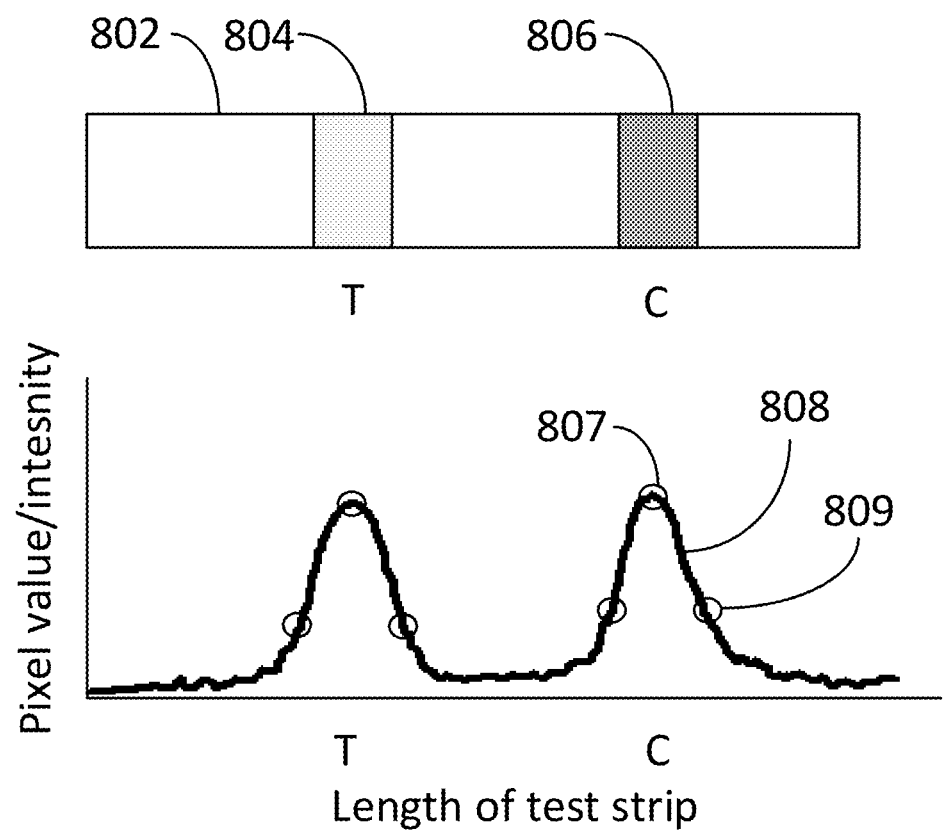
FIG. 8 depicts an image schematic representation of normalized RGB pixel values of a Test and Control image taken from a test strip image baseline determination consistent with embodiments of the present invention.

FIG. 8 depicts an Image Schematic representation of normalized RGB pixel values of a Test and Control image taken from a test strip image. Here, a sample material is applied to a test strip 802, which after some time becomes developed revealing the "T" and "C" lines 804 and 806. The graph 808 represents the relative RGB pixel density of the test region 804 and the control region 806. In the graph, test region 804 is normalized to the control region 806 against a constant color background. The Peak-Baseline, wherein the peak 807 and the baseline 809 are depicted with circles on the graph iterate, for the control band 806 and test band 804 are calculated and expressed as it Peak Ratio. The Area under the curve is measured for each test band 804 and control band 806 defined from peak to right and left baseline points expressed as the Area Ratio. The 50/50 waiting of the Test Ratio and the Area Ratios to find the Composite Ratio, which is used for the image schematic and comparison to a standard curve.

Figure 9:
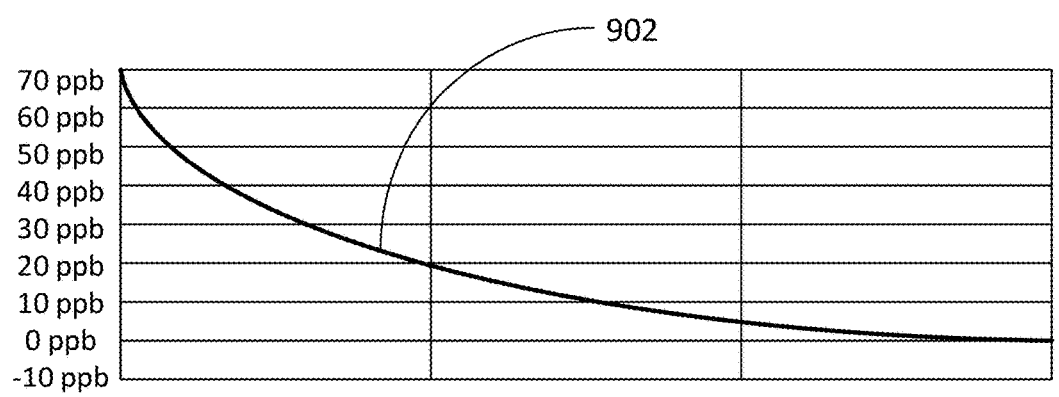
FIG. 9 depicts an example of identifying concentration of a substance by way of fitting a test result on the known curve consistent with embodiments of the present invention.

FIG. 9 depicts an example of identifying concentration of a substance in parts per billion (ppb) by way of fitting a test result on the known curve. In this example, "T" and "C" ratios are obtained for a peanut aflatoxin 2 band lateral flow test. For this test, an image score is generally not obtained until it has been to at least 10% of the total pool of damages that it could be matched against if the image pool size is fixed; otherwise the scores obtained after 100 (or some other substantial number) randomly selected from match pairings of arbitrary sized pool. The results of the scored images may then be used to quantify images by curve fitting and interpolation or predetermined image ratios as standards. The standards may be derived from Test/Control ratios that have been using the modular specimen imaging chamber 102. Once the Test/Control ratio is obtained, it is placed on the appropriate calibration curve (e.g. 100% equals 18 ppb—parts per billion). The standard curve is generated from known standards of multiple calibrations. The results obtained from the imaging notify users of amount that quantifies the analyte.

An alternative method for baseline subtraction, de-trending and background subtraction from a line profile can be accomplished by differentiating the line profile as described above to generate the slope line profile, then transforming the slope line profile by calculating the absolute slope values and replacing the negative slope values with the absolute values. This absolute slope line profile transformation effectively removes background from the line profile. The Test and Control peaks and areas may then be determined and used for the composite ratio calculation.

Embodiments for baseline subtraction method for determining the Composite ratio for quantitative ratiometric image analysis contemplated are used to remove or reduce noise and other artifacts from test and control regions-of-interest of specimen images 712. The defined rectangular region of interest 708 is determined by the placement of the specimen 702 in the illumination chamber top stage module 102 that is positioned in front of the camera 194. Embodiments contemplate the RGB values from 0 to 255 measured by the mobile device camera 194, hardware and software for each pixel in the vertical (Y dimension) or horizontal (X dimension). The two-dimensional planar region of interest can then be transformed into a one-dimensional line with a horizontal or vertical orientation. This dimensional transformation is called a line profile and it establishes the basis for all subsequent quantitative measurements of the region of interest. The first point of the horizontal or vertical line profile is used to establish the starting baseline. The middle point of the line profile is used as a second point to establish the baseline. The last point in the line profile is used as the third point to establish the baseline. A line curve is fit between the first and second points and again between the second and third points. These two curve fits are merged into one curve fit, which is then subtracted from the region of interest line profile. This procedure establishes the baseline pixel as zero and it de-trends the line profile by removing background shadows or noise. The resultant baseline subtracted line profile is the dataset that is used for peak and area.

Figure 10A:
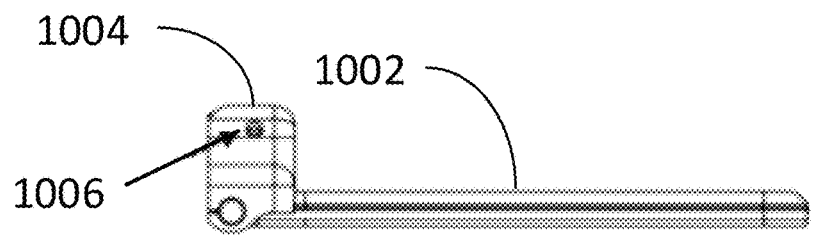
FIGS. 10A-D depicts an optional embodiment of a system for testing colored solutions containing DNA or color indicators in liquid form consistent with embodiments of the present invention.
Figure 10B:
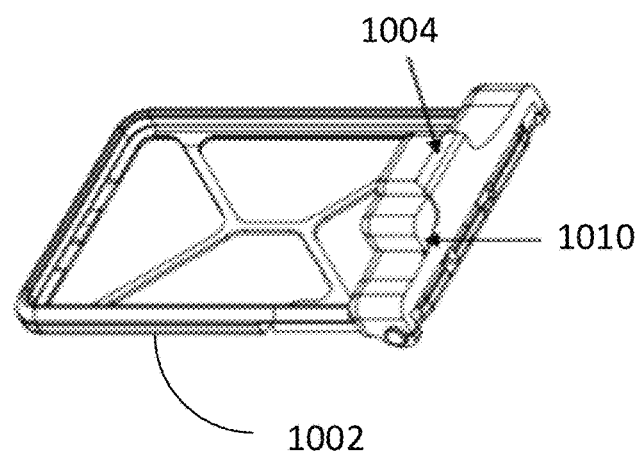
Figure 10C:
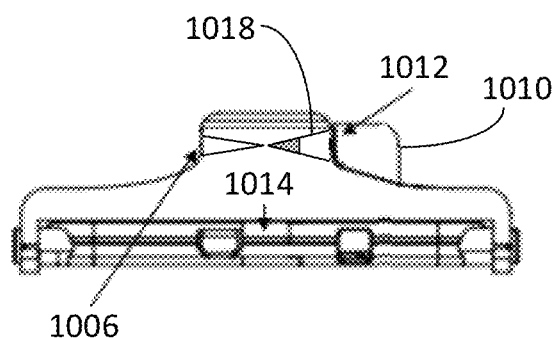
Figure 10D:
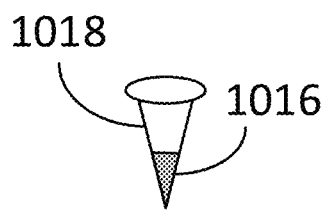

FIG. 10A depicts an optional embodiment to test colored solutions containing DNA or color indicators in liquid form consistent with embodiments of the present invention. As shown, the protective case/tablet holder 1002 is similar to that shown in FIG. 1, however the hood and chamber 1004 possess an external light source 1006. FIG. 10B depicts a different view of the protective case/tablet holder 1002 possesses a sample tube and light cover 1010. FIG. 10C shows the hood in chamber 1004 with a cone shaped liquid sample in a plastic tube 1018 disposed in an accommodating opening in the chamber 1012 and the external light source 1006. For reference, there is a lens 1014 that brings the sample 1016 into focus either by changing the focal length of the forward facing camera 194 and/or magnification of the sample 1016. FIG. 10D depicts a cone shaped plastic tube 1018 containing a liquid sample 1016. One embodiment contemplates the external light being produced by an LED in specific wavelengths such as ultraviolet, or some other specific wavelength in or outside the visual light spectrum. Unlike the other illumination chamber depicted in FIGS. 1-6, illumination chamber of FIG. 10A-D uses an external light, such as an LED, instead of the touch screen 192 to illuminate the sample 1016. As shown in this embodiment, there is a hole for an external light source 1016, such as an LED of any wavelength is abutted against the clear to with 10-100 microliters of liquid contained in the cone shaped plastic tube 1018. The sample is illuminated and the color is measured using the RGB color planes in the image from the front facing camera 194 on the tablet or phone 190. From the image, the RGB values can be quantified for the region of interest of the solution and compared to known standards for the analyte being measured. This can be applied for DNA amplification measurement when combined with a DNA indicating dye. It can also be used to quantify proteins in a solution when combined with the appropriate dyes.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms used herein. For example, though embodiments of the present invention describe a protective case for use with a tablet or cell phone, it is contemplated that other similar devices can be used for biological testing within the scope and spirit of the present invention can be used while still maintaining substantially the same functionality without departing from the scope and spirit of the present invention. The specification and drawings are to be regarded as illustrative and exemplary rather than restrictive. For example, the word "preferably," and the phrase "preferably but not necessarily," are used synonymously herein to consistently include the meaning of "not necessarily" or optionally. "Comprising," "including," and "having," are intended to be open-ended terms.

It will be clear that the claimed invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the claimed invention disclosed and as defined in the appended claims. Accordingly, it is to be understood that even though numerous characteristics and advantages of various aspects have been set forth in the foregoing description, together with details of the structure and function, this disclosure is illustrative only, and changes may be made in detail, especially in matters of structure and arrangement to the full extent indicated by the broad general meaning of the terms in which the appended claims are expressed.

What is claimed is:
1. A test sample apparatus comprising:
  a holder base arranged to accommodate and conform to at least a portion of a handheld electronic device, the handheld electronic device possessing a front surface having an illuminating touchscreen and a camera, the handheld electronic device possessing a back surface and essentially four sides;
  a hood configured to be placed over a portion of the illuminating touchscreen, when placed over the portion of the illuminating touchscreen the hood is configured to collect light from the illuminating touchscreen when activated;

a chamber integrated with the hood adapted to accommodate a chemically activated test strip, the chamber adapted to funnel said light to the chemically activated test strip; and a lens in the hood, the lens adapted to focus the camera on a portion of the chemically activated test strip while the hood is placed over the portion of the illuminating touchscreen.

2. The test sample apparatus of claim 1 wherein the handheld electronic device is in possession of a photograph of the chemically activated test strip taken by the camera while the hood is placed over the portion of the illuminating touchscreen when illuminated.

3. The test sample apparatus of claim 2 wherein the handheld electronic device is adapted to evaluate the photograph.

4. The test sample apparatus of claim 2 wherein the chemically activated test strip possesses fully developed test lines and control lines.

5. The test apparatus of claim 1 wherein the holder base surrounds the four sides and the back surface.

6. The test apparatus of claim 1 further comprising a hinge system that pivots the hood over the portion of the illuminating screen.

7. The test apparatus of claim 1 wherein the lens changes magnification, focal length or both the magnification and the focal length of an image taken by the camera.

8. The test apparatus of claim 1 wherein the handheld electronic device provides a specific light wavelength or wavelengths required to develop the chemically activated test strip.

9. The test apparatus of claim 1 wherein the chemically activated test strip develops biologic samples.

10. The test apparatus of claim 1 wherein the chemically activated test strip is disposed in a strip holder that is engaged with the chamber.

11. A method comprising:
providing a handheld electronic device possessing a front surface having an illuminating touchscreen and a camera;

placing the handheld electronic device in a case that conform to at least a portion of the handheld electronic device, the case does not obstruct the illuminating touchscreen and the camera;

positioning a light collecting hood over a portion of the illuminating touchscreen that when positioned inherently aligns a lens with the camera, the lens comprised by the light collecting hood;

placing a chemically activated test strip in a chamber integrated with the light collecting hood, the lens located between the camera and the chemically activated test strip;

illuminating the chemically activated test strip by illuminating the touchscreen;

taking a picture with the camera of the illuminated chemically activated test strip after the chemically activated test strip is developed; and determining results of the developed chemically activated test strip via the picture retained by the camera.

12. The method of claim 11 further comprising developing the chemically activated test strip via a specific spectrum of light generated by the illuminating touchscreen.

13. The method of claim 11 further comprising locking the light collecting hood to the case prior to the illuminating step.

14. The method of claim 11 further comprising disposing the chemically activated test strip in a tester holder that is placed in the chamber.

15. The method of claim 11 further comprising storing the picture in non-transitory memory in the handheld electronic device.

16. The method of claim 15 wherein the determining step includes comparing intensity of a test line in the picture with a pre-established curve of test line intensities.

17. The method of claim 11 wherein the positioning the light collecting hood over the portion of the illuminating touchscreen is accomplished by pivoting the light collecting hood about at least one hinge.

18. A test sample apparatus comprising:
a protective case adapted to accommodate a handheld electronic device, the handheld electronic device possessing a front surface having an illuminating touchscreen and a camera that are not obstructed by the protective case;

means for positioning a light collecting hood over a portion of the illuminating touchscreen that when positioned inherently aligns a lens with the camera;

means for placing a chemically activated test strip in a chamber integrated with the light collecting hood;

means for illuminating the chemically activated test strip via the handheld electronic device;

means for taking a picture of the illuminated chemically activated test strip; and means for determining results of the chemically activated test strip.

19. The test sample apparatus of claim 18 wherein the light collecting hood is adapted to be locked to the protective case.

20. The test sample apparatus of claim 18 further comprising means for focusing the chemically activated test strip with the camera.

* * * * *